United States Patent
Denat et al.

(10) Patent No.: US 6,534,649 B1
(45) Date of Patent: Mar. 18, 2003

(54) SILICA GEL INCORPORATING POLYAZACYCLOALKANE UNITS COMPRISING MORE THAN SIX NITROGEN ATOMS, PREPARATION PROCESS AND USE

(75) Inventors: Franck Denat, Dijon (FR); Géraud Dubois, Dijon (FR); Raphaël Tripier, Dijon (FR); Roger Guilard, Fontaine les Dijon (FR); Bruno Roux-Fouillet, Dijon (FR)

(73) Assignee: L'Air Liquide, Societe Anonyme a Directoire et Conseil de Surveillance pour l'Etude et l'Exploitation des Procedes Georges Claude, Paris (FR)

( * ) Notice: Subject to any disclaimer, the term of this patent is extended or adjusted under 35 U.S.C. 154(b) by 0 days.

(21) Appl. No.: 09/624,341

(22) Filed: Jul. 24, 2000

(30) Foreign Application Priority Data

Jul. 23, 1999 (FR) .............................. 99 09587

(51) Int. Cl.⁷ .......................... C07F 7/18; C08G 77/04; B01D 53/00; B01J 45/00
(52) U.S. Cl. .................................... 540/452
(58) Field of Search ........................ 540/452

(56) References Cited

U.S. PATENT DOCUMENTS 5,120,443 A    6/1992    Bruening et al. ........... 210/638

FOREIGN PATENT DOCUMENTS

| EP | 0 581 433 | 2/1994 |
|---|---|---|
| FR | 2 774 092 | 7/1999 |
| WO | WO 96/11056 | 4/1996 |
| WO | WO 99/37399 | 7/1999 |
| WO | WO 99/37656 | 7/1999 |

OTHER PUBLICATIONS

Gros et al., "New Silica–gel–bound Polyazacycloalkanes and Characterization of their Copper (II) Complexes Using Electron Spin Resonance Spectroscopy", 1996, *Journal of the Chemical Society, Dalton Transactions*, XP002075424, pp. 1209–1214.

*Primary Examiner*—Bruck Kifle
(74) *Attorney, Agent, or Firm*—Young & Thompson

(57) ABSTRACT

Compound of formula (I):

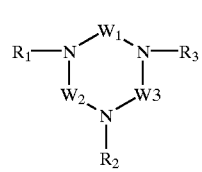

(I)

in which $W_1$, $W_2$ and $W_3$, which are identical or different, each represent, independently of one another, a divalent radical chosen from those represented by the general formula (A):

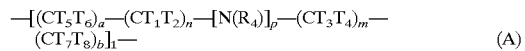

(A)

as defined in the description and in which $R_4$ represents a hydrogen atom, an alkyl radical, a [(hetero)aryl]alkyl radical or a radical represented by the general formula (B), $R_5$—Si $(X_1)(X_2)(X_3)$, as defined in the description, and $R_1$, $R_2$ and $R_3$, which are identical or different, each represent, independently of one another and of $R_4$, a hydrogen atom, an alkyl radical, a [(hetero)aryl]alkyl radical comprising from 7 to 12 carbon atoms or a radical represented by the general formula (B), it being understood that the compound of formula (I) comprises more than six cyclic nitrogen atoms.

1 Claim, No Drawings

SILICA GEL INCORPORATING POLYAZACYCLOALKANE UNITS COMPRISING MORE THAN SIX NITROGEN ATOMS, PREPARATION PROCESS AND USE

BACKGROUND OF THE INVENTION

A subject-matter of the invention is a novel material which can be used in the field of the separation and purification of gases. Current separation techniques, whether cryogenic distillation or adsorption on zeolites, and techniques for the purification of industrial gases by cryogenic or catalytic distillation are not always optimized, either in economic terms or in terms of purity. Many studies have furthermore shown that gases such as oxygen, hydrogen or carbon monoxide react selectively and reversibly with transition metal complexes. Thus, cobalt(II) complexes of cyclam or of cyclene easily fix atmospheric oxygen (Machida R., Kimura E., Kodama M., *Inorg. Chem.*, 1983, 22, 2055–2061) and result in $\mu$-peroxide species in aqueous media. However, the lifetime of the oxygen-comprising complexes in solution is limited as the latter can undergo irreversible decomposition reactions (Martell A. E., Basak A. K., Raleigh C. J., *Pure Appl. Chem.*, 1988, 60, 1325–1329). Furthermore, these species cannot be deoxygenated simply by decreasing the dioxygen partial pressure. An improvement in the reversibility, necessary in a separation process, requires stabilization of the intermediate superoxide species. Grafting the ligand to a solid matrix should, at the same time, slow down the change from the superoxide species to the $\mu$-peroxide species, restrict hydrolysis reactions and facilitate the handling of the active complex (Tsuchida E., Nishide H., *Top. Curr. Chem.*, 1986, 32, 63–99). The incorporation of complexes of cobalt with porphyrins, phthalocyanines or cyclidenes in organic or inorganic polymers, such as silica gels, and the study of the interaction of these materials with oxygen have formed the subject of several studies. Generally, the complex is synthesized in a first stage and then immobilized on the polymer via a dative bond between a nitrogen atom of a pyridine or imidazole unit and the metal (Nishide H., Suzuki T., Kawakami H., Tsuchida E., *J. Phys. Chem.*, 1994, 5084–5088; Cameron J. H., Graham S., *J. Chem. Soc. Dalton Trans.*, 1992, 385–391; Bowman R. G., Basolo F., Burwell Jr. R. L., *J. Am. Chem. Soc.*, 1975, 97, 5125–5129). Another approach consists in attaching, in a first step, the ligand to the polymer via a covalent, bond and in subsequently metallating (Wöhrle D., Gitzel J., Krawczyk G., Tsuchida E., Ohno H., Okura I., Nishisaka T., *J. Macromol. Sci., Chem.*, 1988, A25, 1227–1254; Barnes M. J., Drago R. S., Balkus Jr. K. J., *J. Am. Chem. Soc.*, 1988, 110, 6780–6785). Thus, the grafting to silica gel of tetraazamacrocyclic ligands and the study of the metallation of these materials have been carried out (Gros. C., Rabiet F., Denat F., Brandes S., Chollet H., Guilard R., *J. Chem. Soc. Dalton Trans.*, 1996, 1209–1214). The sol-gel process has been studied in detail (Hench L. L., West J. K., *Chem. Rev.*, 1990, 90, 33–72) and is of major importance in the chemistry of the materials. One of the main advantages of this process is the high homogeneity of the materials obtained, thus conferring specific properties on them. Precursors of alkoxide type are among the most widely used. Thus, the hydrolysis of tetraethoxysilane in solution in an organic solvent, for example an alcohol, results in a colloidal dispersion of particles, which particles result from the polymerization of the precursor and which dispersion is referred to as a sol. This sol changes in the direction of the formation of a gel. The drying of this gel by evaporation results in a xerogel, which can itself be converted into glass or ceramic. More recently, this technique has made possible the preparation of novel organic-inorganic hybrid materials (Corriu R. J. P., Leclercq, D., *Angew. Chem. Int. Ed.*, 1996, 35, 1420–1436; Schubert U., Hüsing N., Lorenz A., *Chem. Mater.*, 1995, 7, 2010–2027). The precursor is then an organic compound carrying one or more endings of trialkoxysilyl [Si(OR$_3$)] or silyl [SiH$_3$] type. Various organic species have been used, such as aromatic compounds, acetylenic units or linear and cyclic amines (Corriu R. J. P., Leclercq D., *Angew. Chem. Int. Ed.*, 1996, 35, 1420–1436; Khatib I. S., Parish R. V., *J. Organomet. Chem.*, 1989, 369, 9–16; Tsuda T., Fujiwara T., *J. Chem. Soc., Chem. Commun.*, 1992, 1659–1661). Battioni et al. have used this route to incorporate manganese and iron porphyrins in a silica gel and have tested the catalytic properties of these novel materials (Battioni P., Cardin E., Louloudi M., Schöllhorn B., Spyroulias G. A., Mansuy D., Traylor T. G., *Chem. Commun.*, 1996, 2037–2038).

SUMMARY OF THE INVENTION

The anchoring of a complex to the polymer via a dative bond between a base and the metal exhibits the advantage of activating the complex and of stabilizing the superoxide species by hindering one of the faces of the complex. However, the bond thus formed is weak. The grafting of the ligand via a covalent bond results, for its part, in a stronger material. Generally, the methods for the incorporation of transition metal complexes in organic or inorganic matrices have to date been unable to result in materials which are compatible with the requirements of process engineering and can thus be used in industrial processes. In particular, the characteristics of such a material must be able to be adjusted in terms of specific surface, of porosity, whether this be the radius, the shape or the size distribution of the pores, and of particle size. The Applicant Company has found that the material which is a subject-matter of the present invention makes it possible to solve the problems set out hereinabove. A subject-matter of the invention is a compound of formula (I):

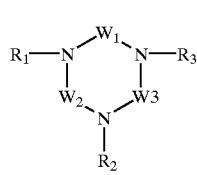

(I)

in which $W_1$, $W_2$ and $W_3$, which are identical or different, each represent, independently of one another, a divalent radical chosen from those represented by the general formula (A):

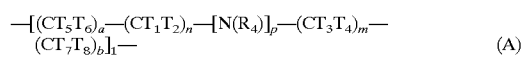

(A)

in which p represents an integer equal to 0 or to 1, 1 represents an integer greater than or equal to 1 and less than or equal to 10 and more particularly less than or equal to 5, n and m, which are identical or different, each represent, independently of one another, an integer less than or equal to 3 and greater than or equal to 1, a and b, which are identical or different, each represent, independently of one another, an integer of less than or equal to 2 and greater than or equal to 0, $T_1$, $T_2$, $T_3$, $T_4$, $T_5$, $T_6$, $T_7$ and $T_8$, which are identical or different, either each represent,independently of one another, a hydrogen atom, a linear or branched alkyl radical comprising from 1 to 15 carbon atoms, or a [(hetero)aryl]alkyl radical comprising from 7 to 12 carbon atoms or $CT_1T_2$ and/or $CT_3T_4$ and/or $CT_5T_6$ and/or $CT_7T_8$ represent a divalent group —(C=O)—, $R_4$ represents a hydrogen atom, a linear or branched alkyl radical comprising from 1 to 15 carbon atoms which is unsubstituted or substituted by one or more functional groups, a [(hetero)aryl]-alkyl radical comprising from 7 to 12 carbon atoms or a radical represented by the general formula (B):

in which $X_1$, $X_2$ and $X_3$, which are identical or different, each represent, independently of one another, a hydrogen atom, a halogen atom or an $OR_6$ radical, in which $R_6$ represents a hydrogen atom or an alkyl radical comprising from 1 to 4 carbon atoms, and $R_5$ represents divalent radical derived from a saturated or unsaturated aliphatic hydrocarbonaceous chain comprising from 1 to 10 carbon atoms, in which chain are optionally included one or more structural links chosen from the arylene group or the —O—, —S—, —O—C(=O)—, —N($R_7$)—, —C(=O)— or —N($R_7$)— fragments, in which $R_7$ represents a hydrogen atom, an aliphatic hydrocarbonaceous radical comprising from 1 to 6 carbon atoms, a benzyl radical or a phenethyl radical, the said chain being unsubstituted or substituted by one or more radicals chosen from halogen atoms, the hydroxyl group, alkyl radicals comprising from 1 to 4 carbon atoms or the benzyl or phenethyl radicals; $R_1$, $R_2$ and $R_3$, which are identical or different, each represent, independently of one another and of $R_4$, a hydrogen atom, a linear or branched alkyl radical comprising from 1 to 15 carbon atoms which is unsubstituted or substituted by one or more functional groups, [(hetero0)aryl]alkyl radical comprising from 7 to 12 carbon atoms or a radical represented by the general formula (B) as defined above, it being understood that the compound of formula (I) comprises more than six cyclic nitrogen atoms.

Mention may be made, as compounds of formula (I) comprising more than six cyclic nitrogen atoms, of, for example, the compounds derived from 1,4,8,11,15,18,22,25-octaazacyclooctacosane, comprising eight cyclic nitrogen atoms, or the compounds derived from 1,4,7,10,13,16,19, 22,25,28,31,34,37,40,43,46-hexadecaazacyclooctatetracontane or from 1,4,8,11,15,18, 22,25,29,32,36,39,43,46,50,53-hexadecaazacyclohexapentacontane, comprising 16 cyclic nitrogen atoms. The term "functional group" denotes in particular, in the definitions of $R_1$, $R_2$, $R_3$ and $R_4$, the carboxyl ($CO_2H$), carboxamido ($CONH_2$), sulpho ($SO_3H$) or dihydrophosphonato ($PO_3H_2$) groups, in the free or esterified form.

A particular subject-matter of the invention is a compound of formula (I) as defined above in which, when $T_1$, $T_2$, $T_3$, $T_4$, $T_5$, $T_6$, $T_7$ and $T_8$ represent a hydrogen atom or an alkyl radical, $T_1$ is identical to $T_2$, $T_3$ is identical to $T_4$, $T_5$ is identical to $T_6$ and $T_7$ is identical to $T_8$ and more particularly a compound of formula (I) as defined above in which, when $T_1$, T2, $T_3$, $T_4$, $T_5$, $T_6$, $T_7$ and T8 represent an alkyl radical, it is the methyl radical.

A more particular subject-matter of the invention is a compound of formula (I) as defined above which is derived from 6,6,13,13,20,20,27,27-octamethyl-1,4,8,11,15,18,22, 25-octaazacyclooctacosane, from 6,6,13,13,20,20,27,27-octamethyl-1,4,8,11,15,18,22,25-octaazacyclooctacosane-2, 3,16,17-tetraone, from 1,4,7,10,13,16,19,22,25,28,31,34,37, 40,43,46-hexadecaazacyclooctatetracontane-2,3,14,15,26, 27,38,39-octaone or from 1,4,8,11,15,18,22,25,29,32,36,39, 43,46,50,53-hexadecaazacyclohexapentacontane-2,3,16,17, 30,31,44,45-octaone.

According to another specific aspect of the present invention, a subject-matter of the latter is the compound of formula (I) as defined above in which $R_1$, $R_2$, $R_3$ and $R_4$, which are identical or different, represent, independently of one another, either a hydrogen atom or a radical of formula ($B_1$):

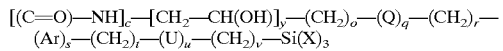

in which o, r, t and v, which are identical or different, each represent, independently of one another, an integer greater than or equal to 0 and less than or equal to 6, c, y, q, s and u, which are identical or different, represent, independently of one another, an integer equal to 0 or to 1, Q and U, which are identical or different, each represent, independently of one another, an oxygen atom, a sulphur atom or one of the —O—CO—, —CO—O—, —NH—CO—, —CO—NH— or —NH— groups, Ar represents an arylene group and in particular a phenylene group, and X represents a hydrogen atom or either of the methoxy or ethoxy radicals, it being understood that, when c and q are equal to 1, the sum y+o is other than zero, that, when q is equal to 1 and when u is equal to 0, the sum r+s+t+v is other than 0, that, when u is equal to 1, v is other than 0, that, when u is equal to 1 and when q is equal to 0, the sum y+o+r+s+t is other than 0, that, when s is equal to 0 and when q and u are each equal to 1, the sum r+t is other than 0, and that the sum c+y+o+r+t+v is less than or equal to 12.

In a preferred alternative form of the present invention, the radical of formula ($B_1$) as defined above is chosen from the 3-(triethoxysilyl)propyl, 3-[[3-(triethoxysilyl)propyl] oxy]-2-hydroxypropyl, [4-[[[3-(triethoxysilyl)propyl] amino]methyl]phenyl]methyl, [4-(triethoxysilyl)phenyl] propyl, 3-oxo-3-[[3-(triethoxysilyl)propyl]oxy]propyl, 2-oxo-2-[[3-(triethoxysilyl)-propyl]amino]ethyl, [[3-(triethoxysilyl)propyl]amino]-carbonyl or [4-(triethoxysilyl) phenyl]methyl radicals.

A very particular subject-matter of the invention is the compounds with the following names: 6,6,13,13 20,20,27, 27-octamethyl-1,4,8,11,15,18,22,25-octakis[[[3-(triethoxysilyl)propyl]amino]carbonyl]-1,4,8,11,15,18,22, 25-octaazacyclooctacosane, 6,6,13,13,20,20,27,27-octamethyl-8,11,22,25-tetrakis[[[3-(triethoxysilyl)propyl] amino]carbonyl]-1,4,8,11,15,18,22,25-octaazacyclooctacosane-2,3,16,17-tetraone,7,10,19,22,31, 34,43,46-octakis[[[3-(triethoxysilyl)-propyl]amino] carbonyl]-1,4,7,10,13,16,19, 22,25,28,31,34,37,40,43,46-hexadecaazacyclooctatetracontane-2,3,14,15,26,27,38,39-octaone, 8,11,22,25,36,39,50,53-octakis[[[3-(triethoxysilyl) propyl]amino]carbonyl]-1,4,8,11,15,18, 22,25,29,32,36,39, 43,46,50,53-hexadecaazacyclohexapentacontane-2,3,16,17, 30,31,44,45-octaone or 6,6,13,13,20,20,27,27-octamethyl-8,11,22,25-tetrakis-[[4-(triethoxysilyl)phenyl]methyl]-1,4, 8,11,15, 18,22,25-octaazacyclooctacosane-2,3,16,17-tetraone.

According to another aspect of the present invention, a subject-matter of the latter is a process for the preparation of the compound of formula (I) as defined above, characterized in that:

a) a compound of formula (C)

in which $X_1$, $X_2$ and $X_3$, which are identical or different, each represent, independently of one another, a hydrogen atom, a halogen atom or an $OR_6$ radical, in which $R_6$ represents a hydrogen atom or an alkyl radical comprising from 1 to 4 carbon atoms, and $R'_5$ represents a divalent radical derived from a saturated or unsaturated aliphatic hydrocarbonaceous chain comprising from 1 to 10 carbon atoms, in which chain are optionally inserted one or more structural links chosen from the arylene group or the —O—, —S—, —O—C (=O)—, —N($R_7$)—C(=O)— or —N($R_7$)— fragments, in which $R_7$ represents a hydrogen atom, an aliphatic hydrocarbonaceous radical comprising from 1 to 6 carbon atoms, a benzyl radical or a phenethyl radical, the said chain being unsubstituted or substituted by one or more radicals chosen from halogen atoms, the hydroxyl group, alkyl radicals comprising from 1 to 4 carbon atoms or the benzyl or phenethyl radicals, and Z represents a functional group capable of reacting with a secondary amine functional group, =N—H, to form an N—C covalent bond, is reacted with a compound of formula (I'):

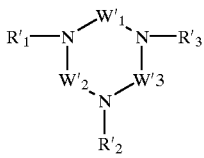

in which $W'_1$, $W'_2$ and $W'_3$, which are identical or different, each represent, independently of one another, a divalent radical chosen from those represented by the general formula (A'):

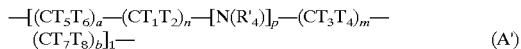

in which a, b, l, p, n, m, $T_1$, $T_2$, $T_3$, $T_4$, $T_5$, $T_6$, $T_7$ and $T_8$ have the same definitions as for the formula (A) as defined above and $R'_4$ represents a hydrogen atom, a linear or branched alkyl radical comprising from 1 to 15 carbon atoms or a [(hetero)aryl]alkyl radical comprising from 7 to 12 carbon atoms, and $R'_1$, $R'_2$ and $R'_3$, which are identical or different, each represent, independently of one another and of $R_4$, a hydrogen atom, a linear or branched alkyl radical comprising from 1 to 15 carbon atoms or a [(hetero)aryl]alkyl radical comprising from 7 to 12 carbon atoms, it being understood that at least one of these cyclic nitrogen atoms is unsubstituted, to form the compound of formula (I) as defined above and, if desired, b) all or a portion of the unsubstituted cyclic nitrogens of the said compound of formula (I) are functionalized, to form a compound of formula (Id), corresponding to the formula (I) as defined above in which at least one of the $R_1$, $R_2$, $R_3$ or $R_4$ radicals represents a —$(CH_2)_w$—C (=O)—V radical in which w and V are as defined above.

The term "functional group capable of reacting with a secondary amine" denotes in particular those which react according to a nucleophilic substitution mechanism, such as, for example, the halogen radicals and in particular the bromo or iodo radicals, or those which react according to an electrophilic addition mechanism, such as, for example, the epoxy functional group, which results in an N—$CH_2$—CH (OH)— fragment; it can also be a free, salified or esterified carboxyl functional group or a $CH_2$=CH— unsaturated group, which results in an N—$CH_2$—$CH_2$— fragment via a reaction of "Michael" type according to a nucleophilic addition mechanism, or an isocyanate functional group, which results in an N—(C=O)—NH— fragment.

These examples are not limiting in nature and it is obvious that any functional group known to a person skilled in the art at the date of filing of the present patent application as being capable of reacting with a secondary amine functional group to form an N—C covalent bond forms an integral part of the description of the present invention.

The compounds of formula ($C_1$):

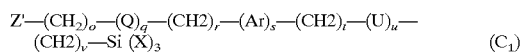

in which o, q, r, s, t, u, v, Q, Ar, U and X have the same definitions as for the formula ($B_1$) as defined above, Z' represents either a halo radical, in particular a bromo radical or an iodo radical, or an oxiran-2-yl group or an ethenyl group or an isocyanato radical, and the sum q+s is equal to 0 or to 1, it being understood that, when q is equal to 1 and when Z' represents a halo radical or an isocyanato radical, o is other than 0, that, when q is equal to 1 and when u is equal to 0, the sum r+s+t+v is other than 0, that, when u is equal to 1, v is other than 0, that, when u is equal to 1 and when q is equal to 0, the sum o+r+s+t is other than 0, that, when s is equal to 0 and when q and u are each equal to 1, the sum r+t is other than 0, and that the sum o+r+t+v is less than 6, in particular (triethoxy)(3-iodopropyl)silane, 2-[[[3-(triethoxysilyl)propyl]oxy]methyl]oxirane, N—[[4-(bromomethyl)phenyl]methyl]—N—[3-(triethoxysilyl) propyl]amine, (triethoxy)[4-(iodomethyl)phenyl]-silane, 3-(triethoxysilyl)propyl propenoate, N—[3-(triethoxysilyl) propyl]bromoacetamide or (triethoxy) (3-isocyanatopropyl) silane, are particularly appropriate in carrying out the process according to the invention.

According to another aspect of the present invention, a subject-matter of the latter is a polysiloxane gel (III) incorporating polyazamacrocycles and metal complexes of these nitrogenous ligands, characterized in that it is capable of being obtained from the hydrolysis of a compound of formula (I) as defined above, resulting in the formation of a polysiloxane gel incorporating non-metallated polyazamacrocycle units (III'), followed by the action of a metal salt on the said gel (III'), and the process for the preparation of the polysiloxane gel (III) thus carried out from the compound of formula (I) as defined above. A more particular subject-matter of the invention is the polysiloxane gel (III,) in which the metal element is chosen from cobalt or copper.

According to another aspect of the present invention, a subject-matter of the latter is a polysiloxane gel (IV) incorporating polyazamacrocycles and metal complexes of these nitrogenous ligands, characterized in that it is capable of being obtained from the action of a metal salt on a compound of formula (I) as defined above, resulting in the formation of an organometallic complex of the said metal with the said compound of formula (I), followed by the hydrolysis of the said organometallic complex, and the process for the preparation of the polysiloxane gel (IV) thus carried out from the compound of formula (I) as defined above. A more particular subject-matter of the invention is the polysiloxane gel ($IV_1$) in which the metal element is chosen from cobalt or copper.

The metal cation involved in the composition of the polysiloxane gel (III) or (IV) is chosen in particular from the cations of U, Pu, Am, Eu, Ce, Cr, Gd, Mn, Fe, Co, Ni, Cu, Zn, Ag, Cd, Au, Hg or Pb and is preferably a $Cu^{++}$ or $Co^{++}$ cation.

In a final aspect of the present invention, a subject-matter of the latter is the use of these metallated hybrid gels as defined above in separating a predetermined gas from a mixture of gases; this use is characterized by bringing the said mixture of gases into contact with one of the metallated hybrid gels (III) or (IV) as defined above under conditions which make possible the absorption of the said gas to be separated, followed by a phase of desorption of the said gas attached to the said gel and by a phase of recovery of the said desorbed gas. This use is preferably applied to the separation of oxygen from the air, either for the purpose of producing pure oxygen or for the purpose of removing oxygen from the air.

The non-metallated gels (III') can be employed to purify liquids which absolutely have to be free from any metal cation, in particular those used in the electronics industry, such as, for example, dilute or concentrated hydrogen peroxide.

The non-metallated gels (III') can also be used to purify gases by adsorption of the undesirable gaseous impurities.

DETAILED DESCRIPTION OF THE INVENTION

The following examples illustrate the invention and in particular the two routes described above for the synthesis, according to a sol-gel process, of novel polysiloxanes incorporating polyazacycloalkanes and metal complexes of these nitrogenous ligands.

As shown in these examples, the variety of the precursors used, the optional addition of tetraalkoxysilane during the gelling stage and the variations in the operating conditions make it possible to obtain materials with variable compositions and variable textures, both in terms of concentration of ligand or of complex in the solid and in terms of porosity and specific surface. Under strictly identical synthesis conditions, the solids obtained exhibit identical characteristics, thus showing good reproducibility of the method.

The advantages of this method thus lie essentially in the possibility of adjusting the characteristics of the material according to the requirements of materials engineering.

Experimental Part

A) Synthesis of the Precursors

The precursors are synthesized under a nitrogen atmosphere. The starting nitrogenous macrocycles comprising 8 or 16 nitrogen atoms are obtained according to the method described in Tripier R, Siri O, Rabiet F, Denat F, Guilard R, *Tetrahedron Lett.*, 40, 1999, 79–82.

EXAMPLE 1

6,6,13,13,20,20,27,27-Octamethyl-1,4,8,11, 15,18, 22 ,25-octakis[[[3-(triethoxysilyl)propyl]-amino] carbonyl)-1,4,8,11,15,18,22,25-octaazacyclooctacosane

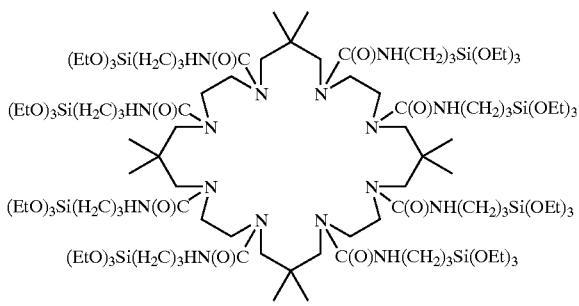

0.69 g (1.35 mmol) of 6,6,13,13,20,20,27,27-octamethyl-1,4,8,11,15,18,22,25-octaazacyclooctacosane is dissolved in 20 cm³ of anhydrous tetrahydrofuran (THF) in a 200 cm³ Schlenk tube. 3.2 g (12.9 mmol) of (3-isocyanatopropyl) triethoxysilane are rapidly added. The reaction mixture is stirred at room temperature for 12 hours. After evaporating the solvent, the solid obtained is washed twice with 50 cm³ of anhydrous pentahe. 1.97 g of the expected compound are obtained in the form of a white powder.

Yd=60%. ¹H NMR (200 MHz, CDCl₃) (δ in ppm),0.61 (m, 16H), 0.93 (m, 24H), 1.19 (t, 72H), 1.6–1.8 (m, 32H), 3.1–3.2 (m, 32H), 3.79 (q, 48H).

EXAMPLE 2

6,6,13,13,20,20,27,27-Octamethyl-8,11,22,25-tetrakis [[3-(triethoxysilyl)propyl]amino]carbonyl]-1,4,8,11,15,18,22,25-octaazacyclooctacosane-2,3,16, 17-25 tetraone

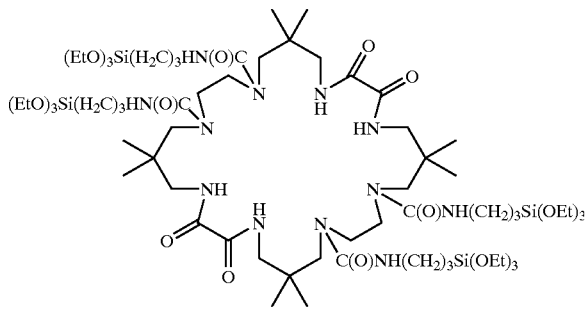

0.5 g (0. 88 mmol) of 6,6,13,13,20,20,27,27-octamethyl-1,4,8,11,15,18,22,25-octaazacyclooctacosane-2,3,16,17-tetraone and 50 cm³ of anhydrous THF are introduced into a 200 cm³ Schlenk tube. 0.92 g (3.7 mmol) of 3-isocyanatopropyltriethoxysilane is rapidly added. The reaction mixture is stirred at room temperature for 7 h. The solid obtained after evaporating the solvent is treated as in Example 1. 1.11 g of the expected compound are thus obtained in 10 the form of a white powder. Yd=81%.

¹H NMR (500 MHz, d₆-DMSO) (δ in ppm), 0. 50 (m, 8H), 0.72 (m, 24H), 1.08 (t, 36H), 1.44 (m, 8H), 2.8–3.3 (m, 32H), 3.67 (q, 24H).

¹³C NMR (125 MHz, d₆-DMSO) (δ in ppm), 8.3, 19.0, 24.4, 38.7, 44.1, 46.5, 58.5, 159.2, 160.8. Elemental analysis for $C_{68}H_{140}N_{12}O_{20}Si_4$:

|  | C | H | N |
| --- | --- | --- | --- |
| Calculated | 52.4% | 9.1% | 10.8% |
| Found | 51.7% | 8.9% | 10.8% |

EXAMPLE 3

7,10,19,22,31,34,43,46-Octakis[[[3-(triethoxysilyl)propyl]amino]carbonyl]-1,4,7,10,13,16,19, 22,25,28, 31,34,37,40,43,46-hexadecaazacyclooctatetracontane-2,3,14,15,26,27, 38,39-octaone

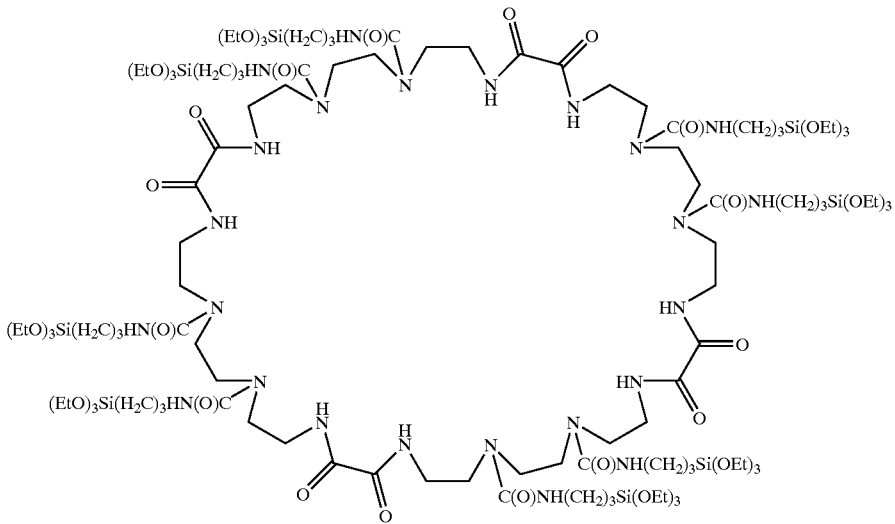

0.37 g (0.46 mmol) of 1,4,7,10,13,16,19,22,25, -28,31, 34,37,40,43,46-hexadecaazacyclooctatetracontane-2,3,14, 15,26,27,38,39-octaone and 50 cm$^3$ of anhydrous THF are introduced into a 200 cm$^3$ Schlenk tube. 0.963 g (3.9 mmol) of 3-isocyanatopropyltriethoxysilane is rapidly added. The reaction mixture is brought to reflux for 12 h. The solid obtained after evaporating the solvent is treated as in Example 1. 0.80 g of the expected compound is obtained in the form of a white powder. Yd=62%.

$^1$H NMR (200 MHz, CDCl$_3$) (δ in ppm), 0.62 (m, 16H), 1.19 (t, 72H), 1.61 (m, 16H), 3.1–3.5 (m, 64H), 3.79 (q, 48H).

Elemental Analysis for $C_{112}H_{232}N_{24}O_{40}Si_8$:

|  | C | H | N |
| --- | --- | --- | --- |
| Calculated | 48.4% | 8.4% | 12.1% |
| Found | 45.0% | 7.8% | 13.9% |

EXAMPLE 4

8,11,22,25,36,39,50,53-Octakis[[[3-(triethoxysilyl)propyl]amino]carbonyl]-1,4,8,11,15, 18,22,25,29,32, 36,39,43,46,50,53-hexadecaazacyclohexapentacontane-2,3,16,17,30,31, 44,45-octaone

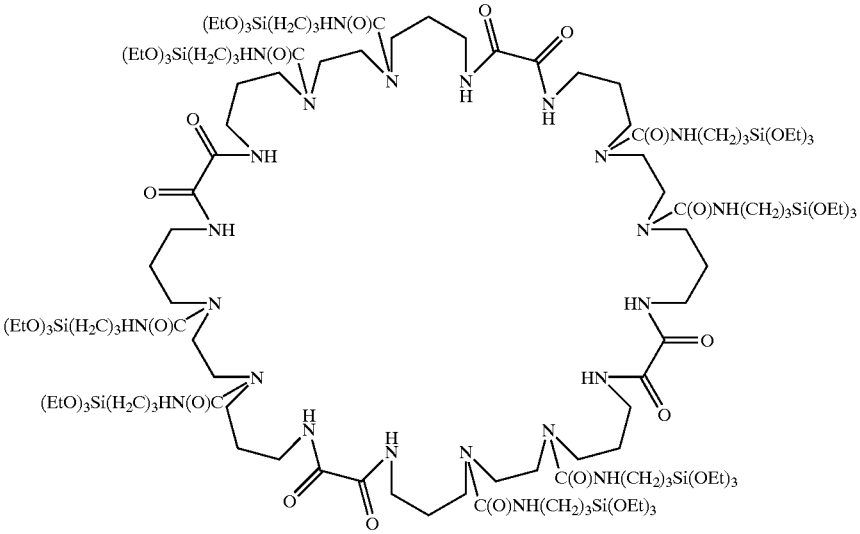

0.5 g (0.55 mmol) of 1,4,8,11,15,18,22,25, -29,32,36,39, 43,46,50,53-hexadecaazacyclohexapentacontane-2,3,16,17, 30,31,45,46-octaone and 100 cm$^3$ of anhydrous THF are introduced into a 200 cm$^3$ Schlenk tube. 1.14 g (4.6 mmol) of 3-isocyanatopropyltriethoxysilane are rapidly added and the reaction mixture is brought to reflux for 12 h. The solid obtained after evaporating the solvent is treated as in Example 1. 1.10 g of the expected compound are obtained in the form of a white powder. Yd=70%.

$^1$H NMR (200 MHz, CDCl$_3$) (δ in ppm), 0.62 (m, 16H), 1.14 (t, 72H), 1.5–1.8 (m, 32H), 3.0–3.3 (m, 64H), 3.75 (q, 48H).

Elemental Analysis for $C_{120}H_{248}N_{24}O_{40}Si_8$:

|  | C | H | N |
|---|---|---|---|
| Calculated | 49.8% | 8.7% | 11.6% |
| Found | 46.6% | 8.3% | 13.1% |

EXAMPLE 5

6,6,13,13,20,20,27,27-Octamethyl-8,11,22,25-tetrakis[[4-(triethoxysilyl)phenyl]methyl]-1,4,8,11, 15,18,22,25-octaazacyclooctacosane-2,3,16,17-tetraone

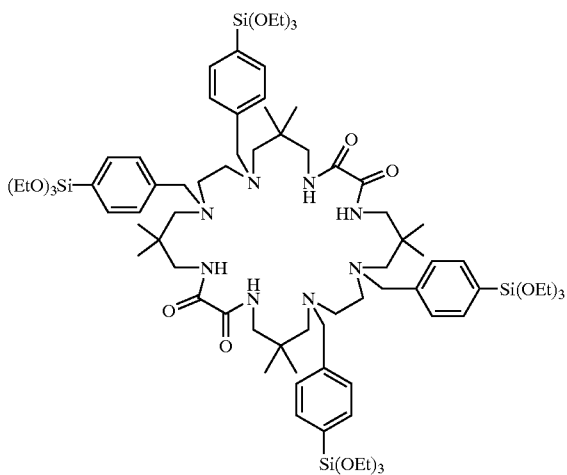

1 g (1.76 mmol) of 6,6,13,13,20,20,27,27-octamethyl-1, 4,8,11,15,18,22,25-octaazacyclooctacosane-2,3,16,17-tetraone, 2.07 g (0.015 mol) of K$_2$CO$_3$ and 30 cm$^3$ of anhydrous THF are introduced into a 200 cm$^3$ Schlenk tube. 2.67 g (7 mmol) of triethoxy[(4-iodophenyl)methyl]silane are added dropwise. The reaction mixture is stirred at room temperature for 12 h and then brought to reflux for 3 h. After returning to room temperature, the residual solid (K$_2$CO3) is filtered off and washed with 2 times 20 cm$^3$ of anhydrous THF. The solvent is evaporated and 2.6 g of the expected compound are obtained in the form of a slightly yellow powder. Yd=94%.

$^1$H NMR (500 MHz, CDCl$_3$) (δ in ppm), 0.8–0.9 (m, 24H), 1.22 (t, 36H), 2.2–3.7 (m, 32H), 3.83 (q, 24H), 7.2–7.6 (m, 16H) $^{13}$C NMR (125 MHz, CDCl$_3$) (δ in ppm) 18.6, 23.9, 37.5, 49.5, 59.1, 62.5, 129.1, 135.3, 160.4.

B)—Synthesis of the Gels

One of the precursors prepared in Examples 1 to 5, the solvent, the necessary amount of water (i.e. 1.5 equivalents with respect to the number of silicon atoms) and the catalyst are placed, in this order, in a pill machine. The gelling time Tg is measured from the moment when all the reactants have been introduced.

The gels obtained are subsequently subjected to ageing for 5 days at room temperature, they are then milled, then washed with ethanol and then with diethyl ether, and finally dried at 100° C. under a pressure of 20 mmHg for 12 h.

C)—Synthesis of the Cogels:

The cogels are synthesized and treated as described above but adding 10 equivalents of tetraethoxysilane (TEOS) to the precursor from the start. The amount of water necessary for the hydrolysis is calculated by adding 1.5 equivalents with respect to the number of silicon atoms present in the precursor to 2 equivalents with respect to the TEOS.

EXAMPLE 6

Preparation of a Gel of the Compound Prepared in Example 1 (Gel 6)

The gel is obtained from 0.5 g (0.2 mmol) of the precursor prepared in Example 1, from 1.4 cm$^3$ of THF, from 0.07 cm$^3$ of water and from 0.2 cm$^3$ of a 0.1 molar solution of TBAF (tetrabutylammonium fluoride) in THF.

The gelling time Tg is 4 days at 19° C. After the treatment, 0.31 g of gel are obtained in the form of a white powder.

CP-MAS $^{29}$Si NMR (δ in ppm), −45, −49, −58, −67.

CP-MAS 13C NMR (δ in ppm), 9.6, 18.9, 24.6, 40–56, 58.5, 89.9, 159.8.

Elemental Analysis for $C_{60}H_{104}N_{16}O_{20}Si_8$

|  | C | H | N |
|---|---|---|---|
| Calculated | 45.2% | 6.6% | 14.1% |
| Found | 42.9% | 7.9% | 11.9% |

BET analysis: Specific surface<10 m2/g

EXAMPLE 7

Preparation of a Cogel of the Compound Prepared in Example 1 (Cogel 7)

The cogel is obtained from 0.5 g (0.2 mmol) of the precursor prepared in Example 1, from 0.21 g (1 mmol) of TEOS, from 1.2 cm$^3$ of THF, from 0.079 cm$^3$ of water and from 0.2 cm$^3$ of a 0.1 molar solution of TBAF in THF. The gelling time Tg is 4 days at 19° C. After treatment, 0.38 g of cogel is obtained in the form of a white powder.

CP-MAS $^{29}$Si NMR (δ in ppm), −46, −58, −64, −100, −110.

CP-MAS C NMR (δ in ppm), 10.0, 19.2, 24.3, 40–56, 58.5, 92.4, 160.2. BET analysis: Specific surface<10 m$^2$/g

EXAMPLE 8

Preparation of a Gel of the Compound Prepared in Example 2 (gel 8)

The gel is obtained from 0.7 g (0.45 mmol) of the precursor prepared in Example 2, 6.3 cm$^3$ of THF, 0.05 cm$^3$ of water and 0.45 cm$^3$ of a 0.1 molar solution of TBAF in THF. Tg=1 day at 19° C. After treatment, 0.44 g of gel are obtained in the form of a white powder.

CP-MAS 29Si NMR (δ in ppm), −45, −59, −65.

CP-MAS $^{13}$C NMR (δ in ppm), 11.1, 18.9, 24.8, 38.4, 46.6, 58.6, 94.9, 160.6.

Elemental Analysis for $C_{44}H_{80}N_{12}O_{14}Si_4$

|  | C | H | N |
|---|---|---|---|
| Calculated | 47.5% | 7.3% | 15.1% |
| Found | 47.7% | 8.1% | 14.3% |

BET Analysis: Specific Surface<10 $m^2$/g

EXAMPLE 9

Preparation of a Gel of the Compound Prepared in Example 3 (Gel 9)

The gel is obtained from 0.6.g (0.263 mmol) of the precursor prepared in Example 3, 6.2 $cm^3$ of THF, 0.07 ml of water and 0.2 $cm^3$ of a 0.1 molar solution of TBAF in THF. Tg=15 days at 19° C. After treatment, 0.35 g of gel are obtained in the form of a white powder.

CP-MAS $^{29}$Si NMR (δ in ppm), −44, −52, −58, −67.

CP-MAS 13C NMR (δ in ppm), 11.2, 18.9, 24.4, 40–46, 58.8, 94.5, 160.7.

Elemental Analysis for $C_{64}H_{112}N_{24}O_{28}Si_8$

|  | C | H | N |
|---|---|---|---|
| Calculated | 40.7% | 6.0% | 17.8% |
| Found | 39.6% | 6.9% | 14.9% |

BET Analysis: Specific Surface<10 $m^2$/g

EXAMPLE 10

Preparation of a Gel of the Compound Prepared in Example 4 (Gel 10)

The gel is obtained from 0.5 g (0.173 mmol) of the precursor prepared in Example 4, 6.9 $cm^3$ of methanol, 0.037 $cm^3$ of water and 0.173 $cm^3$ of a 0.1 molar solution of TBAF in THF. Tg<1 day at 20° C. After treatment, 0.31 g of gel are obtained in the form of a white powder.

CP-MAS 29Si NMR (δ in ppm), −59, −65.

CP-MAS $^{13}$C NMR (δ in ppm), 11.5, 24.9, 40–46, 95, 160.4.

Elemental Analysis for $C_{72}H_{128}N_{24}O_{28}Si_8$

|  | C | H | N |
|---|---|---|---|
| Calculated | 43.2% | 6.5% | 16.8% |
| Found | 40.8% | 6.5% | 15.5% |

BET Analysis: Specific surface<10 $m^2$/g

EXAMPLE 11

Preparation of a Gel of a Compound Prepared in Example 5 (Gel 11)

The gel is obtained from 1.5 g (0.951 mmol) of the precursor prepared in Example .5, 10 $cm^3$ of THF, 0.103 $cm^3$ of water and 0.095 $cm^3$ of a 0.1 molar solution of TBAF in THF. Tg<1 day at 19° C. After treatment, 1.16 g of gel are obtained in the form of a white powder.

BET Analysis: Specific surface<10 $m^2$/g

D)—Metallation of the Gels and Cogels

The gel or the cogel is mixed, in a Schlenk tube and under an argon atmosphere, with 4 equivalents of metal salt ($CuCl_2$) dehydrated beforehand in 10 ml of methanol which has been distilled and dried over a molecular sieve. The reaction mixture is brought to reflux for 12 h and then filtered and washed with 20 $cm^3$ of methanol (10, then 2×5 $cm^3$). The number of milliequivalents of copper sequestered, measured by X-ray fluorescence, makes it possible to determine a metallation yield.

EXAMPLE 12

Metallation of Gel 6

105 mg of a light green powder are obtained from 100 mg of gel 6 and from 33.6 mg of $CuCl_2$. Metallation yd=18%.
BET Analysis: Specific surface<10 $m^2$/g.

Volume of dioxygen $V_{O_2}$ chemisorbed after treatment for 4 h at 250° C.: 1.18 Scc/g (50% oxygenation).

EXAMPLE 13

Metallation of Cogel 7

105 mg of light green powder are obtained from 100 mg of cogel and from 28 mg of $CuCl_{12}$. Metallation Yd=23%.
BET Analysis: Specific surface<10 $m^2$/g.

EXAMPLE 14

Metallation of Gel 11

390 mg of green-brown powder are obtained from 320 mg of gel 11 and 161 mg of $CuCl_2$. Metallation Yd=97% (1.378 mmol/g).
BET Analysis: Specific surface<10 $m^2$/g.

Volume of nitrogen ($V_{N_2}$)physisorbed after treatment for 12 h at 250° C.: 0.

$V_{O_2}$ chemisorbed after treatment for 2h 30 at 150° C.: 1.24 Scc/g (8% oxygenation).

$V_{O_2}$ chemisorbed after treatment for 5h at 250° C.: 2.73 Scc/g (18% oxygenation).

$V_{O_2}$ chemisorbed after treatment for 10h at 250° C.: 3.46 Scc/g (22% oxygenation).

$V_{O_2}$ chemisorbed after treatment for 7h at 250° C.: 3.67 Scc/g (24% oxygenation).

What is claimed is:

1. A compound selected from the group consisting of:
   6,6,13,13,20,20,27,27-octamethyl-1,4,8,11,15,18,22,25-octakis[[[3-(triethoxysilyl)propyl]amino]carbonyl]-1,4,8,11,15,18,22,25-octaazacyclooctacosane,
   6,6,13,13,2,0,20,27,27-octamethyl-8,11,22,25-tetrakis[[[3-(triethoxysilyl)propyl]amino]carbonyl]-1,4,8,11,15,18,22,25-octaazacyclooctacosane-2,3,16,17-tetraone,
   7,10,19,22,31,34,43,46-octakis[[[3-(triethoxysilyl)-propyl]amino]carbonyl]-1,4,7,10,13,16,19,22,25,28,31,34,37,40,43,46-hexadecaazacyclooctatetracontane-2,3,14,15,26,27,38,39-octaone,
   8,11,22,25,36,39,50,53-octakis[[[3-(triethoxysilyl)-propyl]amino]carbonyl]-1,4,8,11,15,18,22,25,29,32,-36,39,43,46,50,53-hexadecaazacyclohexapentacontane-2,3,16,17,30,31,44,45-octaone and
   6,6,13,13,20,20,27,27-octamethyl-8,11,22,25-tetrakis[[4-(triethoxysilyl)phenyl]methyl]-1,4,8,11,15,18,22,25-octaazacyclooctacosane-2,3,16,17-tetraone.

* * * * *